United States Patent [19]

Braksmayer et al.

[11] 4,287,119

[45] Sep. 1, 1981

[54] 3-HYDROXYALKYL PHOSPHINE OXIDE FLAME RETARDANT COMPOSITIONS

[75] Inventors: Diza P. Braksmayer; Syed N. Hussain, both of Plainsboro, N.J.

[73] Assignee: FMC Corporation, Philadelphia, Pa.

[21] Appl. No.: 118,172

[22] Filed: Feb. 4, 1980

[51] Int. Cl.³ .................................................. C08K 5/53
[52] U.S. Cl. ................................. 260/45.95 L; 568/14
[58] Field of Search ....................... 260/606.5, 45.95 L

[56] References Cited

U.S. PATENT DOCUMENTS

| | | | |
|---|---|---|---|
| 3,076,034 | 1/1963 | Gordon | 260/45.95 L |
| 3,099,684 | 7/1963 | Rauhut et al. | 260/185 |
| 3,267,149 | 8/1966 | Garner | 260/606.5 |
| 3,269,963 | 8/1966 | Ilgemann et al. | 260/3.8 |
| 3,306,937 | 2/1967 | Clampitt et al. | 260/606.5 |
| 3,341,625 | 9/1967 | Gillham et al. | 260/887 |
| 3,346,647 | 10/1967 | Garner | 260/606.5 |
| 3,434,981 | 3/1969 | Baranauckas et al. | 260/606.5 |
| 3,489,811 | 1/1970 | Drucker et al. | 260/606.5 |
| 3,629,365 | 12/1971 | Gardner et al. | 260/857 PE |
| 3,654,342 | 4/1972 | Gillham et al. | 260/468.8 |
| 3,666,543 | 5/1972 | Maier | 260/606.5 |
| 3,683,028 | 8/1972 | Hans | 260/606.5 P |
| 3,716,580 | 2/1973 | Maier | 260/606.5 |
| 3,736,349 | 5/1973 | Gillham | 260/136 |
| 3,931,104 | 1/1976 | Luders et al. | 260/45.85 R |
| 3,948,980 | 4/1976 | Dettmier et al. | 260/488 R |
| 3,970,636 | 7/1976 | Hardy et al. | 260/45.8 NE |
| 4,007,229 | 2/1977 | Hechenbleikner | 260/606.5 P |
| 4,056,571 | 11/1977 | Kleiner | 260/568 E |
| 4,087,408 | 5/1978 | Moedritzer | 260/47 P |

FOREIGN PATENT DOCUMENTS 2605307 8/1976 Fed. Rep. of Germany .
1028158 5/1966 United Kingdom .

Primary Examiner—V. P. Hoke
Attorney, Agent, or Firm—Robert W. Kell; Frank Ianno

[57] ABSTRACT

Thermoplastic polyphenylene oxide compositions such as polyphenylene oxide that has been modified with high impact polystyrene are rendered fire retardant by the addition of an effective amount of a 3-hydroxyalkyl phosphine oxide such as n-butyl bis(3-hydroxypropyl) phosphine oxide.

24 Claims, No Drawings

3-HYDROXYALKYL PHOSPHINE OXIDE FLAME RETARDANT COMPOSITIONS

The present invention relates to thermoplastic polyphenylene oxide polymers which are rendered flame retardant by having combined therewith an effective amount of a 3-hydroxyalkyl phosphine oxide.

The polyphenylene ethers are known and described in numerous publications including U.S. Pat. Nos. 3,306,874 and 3,306,875 of Allan S. Hay and U. S. Pat. Nos. 3,257,357 and 3,257,358 of Gelu Stoeff Stamatoff. The high molecular weight polymers are high performance engineering thermoplastics possessing relatively high melt viscosities and softening points—i.e., in excess of 275° C., and are useful for many commerical applications requiring high temperature resistance including formation of film, fiber and molded articles.

The combination of polyphenylene oxide ethers with polystyrene and modified polystyrene is also known and described in U.S. Pat. No. 3,385,435. The preferred polystyrenes are the high impact polystyrenes such as the styrene-acrylonitrile copolymers and styrene-acrylonitrile-butadiene copolymers.

In general, compositions containing from 35 to 85 percent by weight polyphenylene oxide and from 65 to 15 percent by weight of a polystyrene resin exhibit the best overall combination of properties and these compositions are preferred. Such compositions are referred to in this specification and in the claims as "polyphenylene oxide compositions".

With the current and future federal requirements obligating automotive manufacturers to improve the efficiency of their product and reduce fuel consumption, there is a substantial growth in the use of engineering plastics as a replacement for metal to achieve weight reduction. The use of polyphenylene oxide compositions in the transportation, electrical/electronic and appliance categories accounts for a majority of its volume, and polyphenylene oxide compositions are the dominant engineering thermoplastic in appliance use. Such compositions are in general, characterized as being relatively stable thermally upon long exposure to processing temperatures and shear. Upon exposure to flame, however, they burn quite readily as would be anticipated from their relative high styrene content. There is a substantial and increasing demand for flame retardant polyphenylene oxide compositions.

To improve flame retardant characteristics, polyphenylene oxide compositions have been compounded with flame retardant additives, i.e., aromatic halogen compounds plus aromatic phosphates as described in U.S. Pat. No. 3,639,506. A preferred composition in accordance with that teaching comprises from 20 to 80% by weight of poly(2,6-dimethyl-1,4-phenylene) ether, 20 to 80% by weight of a high impact polystyrene (styrene modified with rubber) and from 3 to 25 parts by weight per 100 parts by weight of the polyphenylene oxide composition of a flame retardant combination of 1 part triphenyl phosphate and 3 to 4 parts of a heavily chlorinated biphenyl. U.S. Pat. No. 4,154,775 states that cyclic phosphates are, by themselves, an effective, non-plasticizing flame retardant additive for polyphenylene oxide compositions. Such additives, however, frequently degrade or cause degradation under processing conditions (extrusion at about 250° C.) resulting in poor mechanical performance of the thermoplastic polyphenylene oxide compositions themselves.

The known flame retardants for polyphenylene oxide compositions suffer generally from one or more deficiencies including low compatibility, low thermal stability or poor fire retardant behavior in molded polyphenylene oxide compositions. Additionally, a serious problem posed by aromatic halogen flame retardants in polyphenylene oxide compositions is attributable to acid formation, either due to or arising from light exposure or thermal degradation with the released acid then attacking metal components in end-use applications. Some aromatic halogen compounds are contraindicated as fire retardant additives due to toxicity problems of the compound, i.e., mutagenicity.

The present invention is predicated upon the discovery that the addition of a small but effective amount of a 3-hydroxyalkyl phosphine oxide having the formula:

wherein $R_1$ may be the same or different radicals selected from the group consisting of hydrogen and the methyl radical, $R_2$ is an alkyl radical of 4 to 8 carbon atoms and n is either zero or one, to a thermoplastic polyphenylene oxide composition substantially improves the flame retardant properties of the polyphenylene oxide composition. The addition of the 3-hydroxyalkyl phosphine oxide to the polyphenylene oxide composition in the amount required to improve flame retardant properties does not adversely modify the physical properties of the polyphenylene oxide composition to a point where its commerical use is impaired. The 3-hydroxyalkyl phosphine oxides described above are readily compatible with the polyphenylene oxide composition and effective when added in small quantities, i.e., 4–10 parts per hundred. Particularly preferred compositions are flame retardant polyphenylene oxide compositions to which have been added from about 4 to about 7 parts per hundred of a 3-hydroxyalkyl phosphine oxide.

The flame resistant polyphenylene oxide composition and 3-hydroxyalkyl phosphine oxide blends of the present invention are particularly advantageous for use in appliances, business machines, terminal strips, connectors and blocks.

The 3-hydroxyalkyl phosphine oxides of the present invention are more soluble in water than in polar organic solvents such as chloroform. Such 3-hydroxyalkyl phosphine oxides combine high compatibility in polyphenylene oxide compositions with high thermal stability and excellent fire retardant efficiency either alone or in combination with organohalogen products.

The merits that may be attributed to the 3-hydroxyalkyl phosphine oxide flame retardant (relative to conventional flame retardant agents in present use) include no corrosion, high ultaviolet stability, non-toxicity and minimal adverse change in the physical properties of the polymer. The heat distortion temperature of the polyphenylene oxide composition is not appreciably effected by the addition thereto of 5–7 parts per hundred of a phosphine oxide flame retardant. Particularly advantageous are the alkyl bis(3-hydroxyalkyl) phosphine oxides such as butyl bis(3-hydroxypropyl) phosphine oxide which is compatible with polyphenylene oxide and polystyrene polymers and has improved mixing parameters that reduce polymer degradation by lowering the processing temperature. Also useful as flame retardant additives are the tris(3-hydroxyalkyl) phosphine oxides such as tris(3-hydroxypropyl) phosphine oxide, tris(2-methyl-3-hydroxypropyl) phosphine oxide and mixtures of the same.

3-Hydroxyalkyl phosphine oxides may be prepared by first reacting a 3-hydroxy- 1,2-unsaturated olefin such as allyl alcohol with phosphine in the presence of a free radical catalyst as described in U.S. Pat. No. 3,489,811. We have discovered that the use of stoichiometric quantities of reactants (or as little as 4% excess alcohol) reduce the formation of higher molecular weight by-products. The 3-hydroxyalkyl phosphine obtained by this process is readily converted to the corresponding phosphine oxide by oxidation with hydrogen peroxide.

An example of phosphine oxide useful as fire retardant additives in polyphenylene oxide compositions is the tris(3-hydroxypropyl) phosphine oxide, derived from allyl alcohol. These compounds may be added to polyphenylene oxide compositions in amounts of 4 to 10 parts per hundred. Tris(3-hydroxy-2-methylpropyl) phosphine oxide, derived from methallyl alcohol may also be used as a fire retardant additive but is more volatile.

Phosphine oxides having different 3-hydroxyalkyl groups on the phosphorus atom such as:

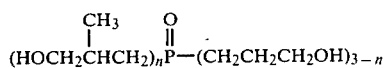

wherein n is either 1 or 2, may be prepared by reacting phosphine with a mixture of allyl and methallyl alcohol and oxidizing the resulting product. Such mixed phosphine oxides are more volatile than the tris(3-hydroxypropyl) phosphine oxide. The relative volatility of this series of compounds (rate of vaporization by thermogravimetric technique) in order of increasing volatility is tris(3-hydroxypropyl) phosphine oxide, bis(3-hydroxypropyl) 2-methyl-3-hydroxypropyl phosphine oxide, tris(2-methyl-3-hydroxypropyl) phosphine oxide and 3-hydroxypropyl bis(2-methyl-3-hydroxypropyl) phosphine oxide. These mixed phosphine oxides as well as physical mixtures of such mixed phosphine oxides with tris(3-hydroxypropyl) phosphine oxide and/or tris(2-methyl-3-hydroxypropyl) phosphine oxide are useful additives having application in the present invention.

The following examples will more fully illustrate the invention.

EXAMPLE I

Preparation of Tris(3-Hydroxypropyl) Phosphine Oxide

Tris(3-hydroxypropyl) phosphine is prepared by the method described in Example 1 of U.S. Pat. No. 3,489,811.

Into a one liter pressure reactor is placed 307 g (5.3 moles) allyl alcohol and 20 ml of a solution containing 3 g azobisisobutyronitrile dissolved in 100 ml of allyl alcohol. The pressure reactor is closed and charged with 36 g (1.06 moles) of phosphine. The reaction mixture is agitated by rocking the reactor for two hours at 80° C. The reaction mixture is permitted to cool to room temperature and the pressure vessel is vented in a hood to release any unreacted phosphine. An additional 20 ml of the azobisisobutyronitrile solution described above is added to the reactor which is closed and the system is again heated to 80° C. and rocked for one hour. The addition of 20 ml of the azobisisobutyronitrile solution is repeated with intermediate agitation at 80° C. for one hour under pressure until all of the azobisisobutyronitrile solution (100 ml) has been added. The contents of the reactor are then heated to 80° C. under pressure and rocked for an additional five hours.

The yellow solution that results from the above reaction is vacuum distilled by heating to about 85° C./133 Pa (1 mm Hg) and maintaining at that temperature and pressure for about four hours to remove volatiles [mono-, and bis(3-hydroxypropyl) phosphine] and unreacted allyl alcohol. The residue remaining in the distillation pot is a clear yellow syrup weighing 184 g.

This non-volatile yellow syrup is dissolved in an equal volume of a 50:50 mixture of isopropanol/methanol and oxidized by stirring with the dropwise solution of a 30% aqueous hydrogen peroxide solution diluted with an equal volume of isopropanol. When the exothermic reaction subsides, the solution of phosphine oxide is tested by adding one drop of the solution to 1 ml of carbon disulfide until no red coloration can be detected visually in the carbon disulfide layer. This indicates complete oxidation of the phosphine to tris(3-hydroxypropyl) phosphine oxide.

Following oxidation with hydrogen peroxide, the solvents (water, isopropanol and methanol) are removed from the reaction product by heating to 65° C. under vacuum. The viscous yellow slush which remains is filtered through a Buchner Funnel to collect 42.4 grams of a white solid that is insoluble in isopropanol at room temperature. The yield, based on the phosphine used is 17.8%. After washing with isopropanol and air drying, the white solid analyses for tris(3-hydroxypropyl) phosphine oxide.

| Found | Theory |
|---|---|
| C = 48.29% | C = 48.21% |
| H = 9.28% | H = 9.38% |
| P = 13.3% | P = 13.84% |

The tris(3-hydroxypropyl) phosphine oxide is evaluated as a fire reactant in polyphenylene oxide compositions (UL 94 Vertical Burn Test). The results are reported in Table I.

In a similar manner 2-methyl-3-hydroxypropyl bis-(3-hydroxypropyl) phosphine oxide may be prepared by reacting one mole of methallyl alcohol and two moles of allyl alcohol with phosphine and oxidizing with hydrogen peroxide. Five parts of this compound with 100 parts of a polyphenylene oxide composition give a UL 94 rating of V-1 (See Table I).

EXAMPLE II n-Butyl-bis(3-Hydroxypropyl) Phosphine Oxide

Into a four liters stainless steel pressure reactor is placed 0.5 g azobisisobutyronitrile dissolved in 600 ml of toluene. The reactor is purged with nitrogen and charged with 112 g (2.0 moles) of butene and 102 g (3.0 moles, 50% excess) phosphine. The reaction mixture is heated and stirred at 85°-90° C. for one hour and maintained at that temperature with stirring while five 20 ml portions of azobisisobutyronitrile solution (5.5 g in 350 ml of toluene) are added at 20 minute intervals over 1 hour 40 minutes. No exotherm is noted during the catalyst addition and the pressure reading dropped from 1.432 MPa (190 psig) (at the time of the first 20 ml catalyst addition) to 1.397 MPa (185 psig) (20 minutes after the last catalyst addition).

The excess phosphine is vented from the reaction vessel and 278 g (4.8 moles, 20% excess) of allyl alcohol and 40 ml of the azobisisobutyronitrile catalyst solution is added to the reaction vessel. No exotherm is observed and heating is continued at 85°–90° C. with stirring and addition of 20 ml of azobisisobutyronitrile every 20 minutes until all of the catalyst solution (350 ml) has been added. The temperature is maintained with stirring at 85°–90° C. for 11 hours. A clear yellow liquid is removed from the reactor and heated to 110° C./133 Pa (1 m Hg) to distill off the volatile materials. The residue is a clear yellow liquid weighing 290.9 grams. This residue is dissolved in an equal volume of isopropanol and oxidized with 30% hydrogen peroxide dissolved in an equal volume of isopropanol as described above in Example I to give 308.2 g of a viscous yellow liquid (after removal of water and isopropanol) containing a small amount of a white suspended solid. The mixture is diluted with chloroform, filtered to remove the white solid, and the chloroform is evaporated to give a clear yellow liquid. The analysis of this liquid product is:

| Found (%) | Calculated for n-butyl bis-(3-hydroxypropyl) phosphine oxide (%) |
|---|---|
| C = 54.50, 54.40 | 54.05 |
| H = 10.21, 10.21 | 10.36 |
| P = 13.28, 13.65 | 13.96 |

This product, which is believed to contain both n-butyl bis(3-hydroxypropyl) phosphine oxide and 3-hydroxypropyl di-n-butyl phosphine oxide, is evaluated as a fire retardant in polyphenylene oxide compositions (UL 94 Vertical Burn Test). The results are reported in Table I.

EXAMPLE III

Preparation of Tris(3-Hydroxy-2-Methylpropyl) Phosphine Oxide

Tris(3-hydroxy-2-methylpropyl) phosphine is prepared by the method described in Example 1 above.

Into a four liter pressure reactor equipped with a stirrer and thermometer is placed 690 g (9.6 moles) of methallyl alcohol and 40 ml of a solution containing 9 g azobisisobutyronitrile dissolved in 200 ml of toluene. The pressure reactor is closed and charged with 96 g (2.8 moles) of phosphine. The reaction mixture is heated with stirring to 60° C. at which temperature the reaction becomes exothermic and the temperature rises to 107° C. Stirring is continued as the temperature subsides from 107° C. to 90° C. and the pressure drops from 803.2 kPa to 349.2 kPa (100 psig to 50 psig). The temperature is maintained at 90° C. with heating and stirring for one hour at which time 50 ml of the azobisisobutyronitrile solution in toluene is pumped into the reactor. The reaction mixture is maintained at 90° C. for one hour with stirring after the second addition of catalyst. The addition of 50 ml of the azobisisobutyronitrile solution is repeated with continuous stirring at 90° C. each hour until all of the azobisisobutyronitrile solution (200 ml) has been added. The contents of the reactor are then stirred while maintaining the temperature at 90° C. for an additional four hours. After the last addition of catalyst solution, the pressure in the reaction vessel has dropped to atmosphere pressure.

The reaction mixture is cooled to room temperature, removed from the reaction vessel and heated up to 35° C. at 266.6 Pa (2 mm Hg) to distill off the volatile components (toluene, methallyl alcohol, mono- and bis-addition products).

The non-volatile colorless liquid residue tris-(3-hydroxy-2-methylpropyl) phosphine weighs 614.7 g. It is dissolved in an equal volume of isopropanol and chilled on ice. The phosphine present in solution is oxidized by the dropwise solution with stirring of a 30% aqueous hydrogen peroxide solution diluted with an equal volume of isopropanol. Inasmuch as the oxidation reaction is exothermic, the course of the reaction may be followed by the temperature increase upon addition of hydrogen peroxide. When the exotherm subsides, a small aliquot of the reaction mixture is tested after each addition of hydrogen peroxide with hydrogen peroxide test paper and by addition of a few drops of the reaction mixture to 1 ml of carbon disulfide. At the end of the oxidation reaction, the observed red color of the carbon disulfide indicative of unoxidized phosphine, disappears and the hydrogen peroxide test paper indicates the presence of hydrogen peroxide.

When the oxidation of the phosphine to phosphine oxide has been completed, the water and isopropanol are removed from the phosphine oxide by heating to 65° C. under vacuum until all volatiles have distilled off. The residue, a clear colorless viscous liquid, weighs 633.5 g and has the following analyses:

| Found (%) | Theory (%) |
|---|---|
| C = 54.59 | C = 54.14 |
| H = 9.35 | H = 10.15 |
| P = 11.1 | P = 11.65 |

The "theory" values are calculated for tris(3-hydroxy2-methylpropyl) phosphine oxide.

Five parts of this compound when added to 100 parts of polyphenylene oxide composition gives a 94 UL Vertical Burn Test rating of V-1 (see Table I).

EXAMPLE IV s-Butyl bis(3-Hydroxypropyl) Phosphine Oxide

Into a 4 liters stainless steel pressure reactor is placed 224 g (4 moles) of mixed 2-butene, 600 ml of toluene, 204 g (6.0 moles, 50% excess) of phosphine and 25 ml of a solution of 4 g azobisisobutyronitrile in 100 ml of toluene. The reaction vessel is heated and stirred at 85° C. to 90° C. for one hour and the remaining azobisisobutyronitrile solution is added in 25 ml portions every 30 minutes until the 100 ml of catalyst solution is used up. The reaction mixture is heated and stirred at 90° C. for 4 hours after the last addition of catalyst solution and then allowed to cool overnight.

The phosphine is vented from the reaction vessel and 487 g (8.4 moles, 5% excess) allyl alcohol is added together with 50 ml of a solution of 8 g azobisisobutyronitrile in 20 ml of toluene. The reaction mixture is heated with stirring at 90° C. with the addition of 50 ml azobisisobutyronitrile catalyst solution every 30 minutes until all 200 ml of solution has been added. Heating and stirring are continued at 90° C. for 4 hours and the reaction vessel is then allowed to cool to room temperature. The liquid from the reaction vessel is heated to 130° C./200 Pa (130° C./1.5 mm Hg) to remove volatile components. The residual product is a greenish liquid weighing 519.3 g.

The residual product is believed to contain both s-butyl bis(3-hydroxypropyl) phosphine and 3-hydroxypropyl di-s-butyl phosphine. It is dissolved in an equal volume of isopropanol and oxidized with 30% hydrogen peroxide in an equal volume of isopropanol as described above in Example 1 until a negative carbon disulfide reading is obtained. The solution of oxidized phosphine is concentrated under reduced pressure to yield a syrupy yellow liquid weighing 555.6 g (99.2% yield on oxidation or a yield of 62.5% based on the starting butene).

This product has the following analyses:

| Found (%) | Calculated for s-butyl bis(3-hydroxypropyl) phosphine oxide (%) |
| --- | --- |
| C = 51.80, 52.06 | 54.05 |
| H = 8.72, 8.94 | 10.36 |
| P = 13.79 | 13.96 |

This is an effective flame retardant when added to polyphenylene oxide compositions in amounts of 4 to 10 parts per hundred.

EXAMPLE V

Effect of 3-Hydroxyalkyl Phosphine Oxide As A Flame Retardant For Polyphenylene Oxide Compositions The phosphine oxides described above in Examples 1 and 3 are added to a polyphenylene oxide composition in the amounts per hundred parts of resin (PHR) indicated in Table I and dispersed throughout the resin. Mixing of the additive and resin is accomplished in a Haake mixer (HAAKE RHEOMIX MODEL 600 with REOCORD EU10 attachment, manufactured by Haake Inc., 244 Saddle River Road, Saddle Brook, N.J. 07662). The mixing takes place at 265° C. at which temperature some of the additive is volatilized. The Underwriter Laboratories rating (Vertical Burn Test) for the various combinations tested is indicated in Table I.

In testing the polyphenylene oxide compositions containing a flame retardant additive, the flame retardant properties are determined following procedures established by the Underwriter Laboratories Bulletin No. 94, STANDARD FOR TESTS FOR FLAMMABILITY OF PLASTIC MATERIALS FOR PARTS IN DEVICES AND APPLIANCES; Second Edition, Second Impression (as revised to Feb. 1, 1974) dated July 30, 1976. Tests were run on 3.175 mm (⅛ inch) specimens and the Vertical Burning Test for classifying Materials 94 V-0, 94 V-1 or 94 V-2 and described in Section 3 of this publication is used. In this test, the V-0 rating indicates the best flame resistance and the V-1 rating indicates less flame resistance.

The invention in its broadest aspects if not limited to the specific details shown and described but departure may be made from such details within the scope of the accompanying claims without departing from the principles of the invention and without sacrificing its chief advantage.

I

Effect of phosphine oxide as a flame retardant in polyphenylene oxide compositions. All quantities are expressed in parts per hundred (PHR).

| A | B | C | D | E | F | G | H |
| --- | --- | --- | --- | --- | --- | --- | --- |
| — | 100 | 5 | — | — | — | — | V-0 |
| 100 | — | 6 | — | — | — | — | V-0 |
| 100 | — | — | 6.5 | — | — | — | V-0 |
| — | 100 | — | 4.25 | — | — | — | V-0 |
| — | 100 | — | — | 8 | — | — | V-1 |
| 100 | — | — | — | — | 5 | — | V-1 |
| 100 | — | — | — | — | — | 5 | V-1 |
| 100 | — | — | — | — | — | — | CB* |
| — | 100 | — | — | — | — | — | CB* |

A = 35 PHR polyphenylene oxide and 65 PHR polystyrene
B = 40 PHR polyphenylene oxide and 60 PHR polystyrene
C = Tris(3-hydroxypropyl) phosphine oxide
D = s-butyl bis(3-hydroxypropyl) phosphine oxide
E = Mixed isopropylphenyl/phenyl phosphate esters
F = Tris(2-methyl-3-hydroxypropyl) phosphine oxide
G = 2-methyl-3-hydroxypropyl bis(3-hydroxypropyl) phosphine oxide
H = UL 94 Vertical Burn Test
CB* = Complete burn

We claim:

1. A polyphenylene oxide composition rendered flame retardant by having combined therewith an effective amount of 3-hydroxyalkyl phosphine oxide having the formula:

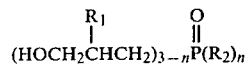

wherein $R_1$ may be the same or a different radical selected from the group consisting of hydrogen, and the methyl radical, $R_2$ is an alkyl radical of 4 to 8 carbon atoms and n is either zero or one.

2. The flame retardant composition of claim 1 wherein the phosphine oxide is tris(2-methyl-3-hydroxypropyl) phosphine oxide.

3. The flame retardant composition of claim 1 wherein the phosphine oxide is tris(3-hydroxypropyl) phosphine oxide.

4. The flame retardant composition of claim 1 wherein the phosphine oxide is n-butyl bis(3-hydroxypropyl) phosphine oxide.

5. The flame retardant composition of claim 1 wherein the phosphine oxide is s-butyl bis(3-hydroxypropyl) phosphine oxide.

6. The flame retardant composition of claim 1 wherein the phosphine oxide is 2-methyl-3-hydroxypropyl bis(3-hydroxypropyl) phosphine oxide.

7. The flame retardant composition of claim 1 wherein said polyphenylene oxide composition contains about 35 parts by weight polyphenylene oxide and about 65 parts by weight of a polystyrene resin.

8. The flame retardant composition of claim 1 wherein said polyphenylene oxide composition contains about 40 parts by weight polyphenylene oxide and about 60 parts by weight of a polystyrene resin.

9. The flame retardant composition of claim 7 wherein the polystyrene present in said composition is a high impact polystyrene.

10. The flame retardant composition of claim 1 to which has been added about 5 parts per hundred of tris(2-methyl-3-hydroxypropyl) phosphine oxide.

11. The flame retardant composition of claim 1 to which has been added about 5 to about 6 parts per hundred of tris(3-hydroxypropyl) phosphine oxide.

12. The flame retardant composition of claim 1 to which has been added about 4.25 to about 6.5 parts per hundred of s-butyl bis(3-hydroxypropyl) phosphine oxide.

13. The flame retardant composition of claim 1 to which has been added about 5 parts per hundred of 2-methyl-3-hydroxypropyl bis(3-hydroxypropyl) phosphine oxide.

14. A method of manufacturing a flame retardant polyphenylene oxide composition which comprises adding thereto an effective amount of a 3-hydroxyalkyl phosphine oxide having the formula:

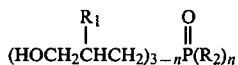

wherein $R_1$ may be the same or a different radical selected from the group consisting of hydrogen and the methyl radical, $R_2$ is an alkyl radical of 4 to 8 carbon atoms and n is either zero or one.

15. The method of claim 14 wherein the phosphine oxide is tris(3-hydroxypropyl) phosphine oxide.

16. The method of claim 14 wherein the phosphine oxide is tris(2-methyl-3-hydroxypropyl) phosphine oxide.

17. The method of claim 14 wherein the phosphine oxide is 2-methyl-3-hydroxypropyl bis(3-hydroxypropyl) phosphine oxide.

18. The method of claim 14 wherein the phosphine oxide is s-butyl bis(3-hydroxypropyl) phosphine oxide.

19. The method of claim 14 wherein said polyphenylene oxide composition contains about 35 parts by weight polyphenylene oxide and about 65 parts by weight of a polystyrene resin.

20. The method of claim 14 wherein said polyphenylene oxide composition contains about 40 parts by weight polyphenylene oxide and about 60 parts by weight of a polystyrene resin.

21. The method of claim 14 wherein the polyphenylene oxide composition contains a high impact polystyrene resin.

22. The method of claim 14 wherein about 5 parts per hundred of tris(2-methyl-3-hydroxypropyl) phosphine oxide is added to said polyphenylene oxide composition.

23. The method of claim 14 wherein about 5 to about 6 parts per hundred of tris(3-hydroxypropyl) phosphine oxide are added to said polyphenylene oxide composition.

24. The method of claim 14 wherein about 4.5 to about 6.5 parts per hundred of s-butyl bis(3-hydroxypropyl) phosphine oxide are added to said polyphenylene oxide composition.

* * * * *